US008137964B2

(12) United States Patent
Akashi et al.

(10) Patent No.: US 8,137,964 B2
(45) Date of Patent: Mar. 20, 2012

(54) METHOD OF PRODUCING THREE-DIMENSIONAL TISSUE AND METHOD OF PRODUCING EXTRACELLULAR MATRIX USED IN THE SAME

(75) Inventors: Mitsuru Akashi, Suita (JP); Yoshiki Sawa, Suita (JP); Michiya Matsusaki, Suita (JP); Yoshio Nakahara, Wakayama (JP)

(73) Assignees: Osaka University, Osaka (JP); Sumitomo Bakelite Co., Ltd., Tokyo (JP)

( * ) Notice: Subject to any disclaimer, the term of this patent is extended or adjusted under 35 U.S.C. 154(b) by 0 days.

(21) Appl. No.: 11/514,468

(22) Filed: Sep. 1, 2006

(65) Prior Publication Data

US 2007/0207540 A1    Sep. 6, 2007

(30) Foreign Application Priority Data

Mar. 2, 2006    (JP) ................................. 2006-056836

(51) Int. Cl.
*C12N 5/06*    (2006.01)
(52) U.S. Cl. ........................................ 435/325; 977/902
(58) Field of Classification Search .................... None
See application file for complete search history.

(56) References Cited

U.S. PATENT DOCUMENTS

2003/0157260 A1* 8/2003 Rubner et al. ................ 427/402

FOREIGN PATENT DOCUMENTS

| EP | 1 602 383 | 12/2005 |
|----|-----------|---------|
| JP | 2816428 | 8/1998 |
| JP | 2947262 | 9/1999 |
| JP | 2004-261024 | 9/2004 |
| JP | 2004-261532 | 9/2004 |
| JP | 2004-261533 | 9/2004 |
| JP | 2005-000608 | 1/2005 |
| JP | 2005-278608 | 10/2005 |

OTHER PUBLICATIONS

Mikos et al. (Biomaterials, 1993; 14(5):323-330).*
Rajagopalan et al. (Tissue Engineering. Jun. 1, 2006; 12(6): 1533-1563).*

(Continued)

*Primary Examiner* — Scott Long
(74) *Attorney, Agent, or Firm* — Hamre, Schumann, Mueller & Larson, P.C.

(57) ABSTRACT

The present invention provides a novel method of producing a three-dimensional tissue by which cell lamination can be carried out easily. According to the method, a three-dimensional tissue in which cell layers are laminated with an extracellular matrix intervening between each pair of the adjacent cell layers is produced by: (A) forming a cell layer on a substrate; (B) bringing the cell layer formed on the substrate into contact with a solution containing a first substance and a solution containing a second substance alternately, thus forming, on the cell layer, an extracellular matrix in which the first substance and the second substance are laminated alternately; and (C) culturing a cell on the extracellular matrix to form a further cell layer. In the present invention, a combination of the first substance and the second substance is (a) a combination of a protein or polymer having an RGD sequence and a protein or polymer that interacts with the protein or polymer having the RGD sequence or (b) a combination of a protein or polymer that is positively charged and a protein or polymer that is negatively charged.

17 Claims, 11 Drawing Sheets

OTHER PUBLICATIONS

Picart et al. (Advanced Functional Materials. 2005; 15(1): 83-94).*
Rajagopalan et al. 2005 NSTI Nanotechnology Conference—abstract.*
Brynda et al. (Langmuir. 2005; 21: 7877-7883).*
Ai et al. (Cell Biochemistry and Biophysics. 2003; 39: 23-43).*
L'Heureux et al. (FASEB Journal. Jan. 1998; 12: 47-56).*
Yamada, et al., "Thermo-responsive polymeric surfaces; control of attachment and detachment of cultured cells", Makromol. Che., Rapid Commun. 11, 271-576 (1990).
Takei, et al., "Role of E-cadherin molecules in spheroid formation of hepatocytes adhered on galactose-carrying polymer as an artificial asialoglycoprotein model", Biotechnology Letters (2005) 27: 1149-1156.
Jessup, et al., "Prospects for Use of Microgravity-Based Bioreactors to Study Three-Dimensional Host-Tumor Interactions in Human Neoplasia", Journal of Cellular Biochemistry 51:290-300 (1993).
Iuchi, et al., "Design of β-sheet peptide with the cell-attachment activity", Journal of Japanese Society for Biometerials (2004), 22, 219-225.
VandeVondele, et al., "RGD-Grafted Poly-L-lysine-*graft*-(polyethylene glycol) Copolymers Block Non-specific Protein Adsorption While Promoting Cell Adhesion", Biotechnology and Bioengineering, vol. 82, No. 7, Jun. 30, 2003.

Deng, et al., "Synthesis and Characterization of RGD Peptide Grafted Poly(ethylene glycol)-*b*-Poly (L-lactide)-*b*-Poly(L-glutamic acid) Triblock Copolymer", Biomacromolecules 2006, 7, 590-596.
Oishi, Shinya, "Structure-Activity Relationship Studies on Cyclic RGD Peptides Utilizing Novel Alkene Dipeptide Isosteres", Yakugaku Zasshi 124(5), 269-277 (2004).
Serizawa, et al., "Stepwise Stereocomplex Assembly of Stereoregular Poly(methylmethacrylate)s on a Substrate", J. Am. Chem. Soc. 2000, 122, 1891-1899.
Serizawa, et al., "Alkaline Hydrolysis of Enantiomeric Poly(lactide)s Sterocomplex Deposited on Solid Substrates", Macromolecules 2003, 36, 1762-1765.
Serizawa, et al., "Alternating Bioactivity of Polymeric Layer-by-Layer Assemblies: Anticoagulation vs Procoagulation of Human Blood", Biomacromolecules 2002, 3, 724-731.
Serizawa, et al., "Enzymatic Hydrolysis of a Layer-by-Layer Assembly Prepared from Chitosan and Dextran Sulfate", Macromolecules 2002, 35, 8656-8658.
Serizawa, et al., "Polymerization within a molecular-scale stereoregular template", Nature (2004), 429, 52-55.
Nakahara, et al., "Controlling of 3D-Cell Organization by Nanostructured-Biodegradable Polymeric Thin Films", Polymer Preprints, Japan (2005), 54, 5207-5208.

* cited by examiner

FIG.4
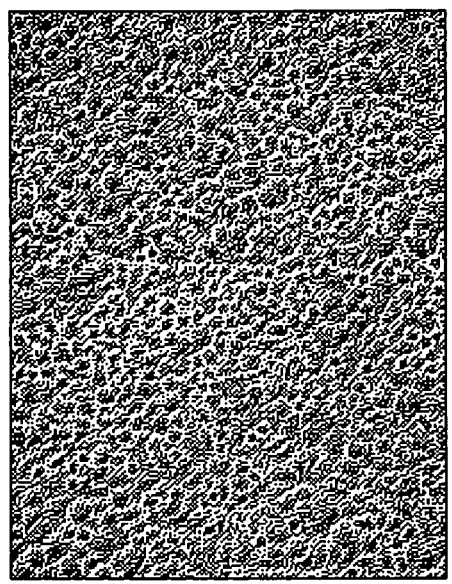
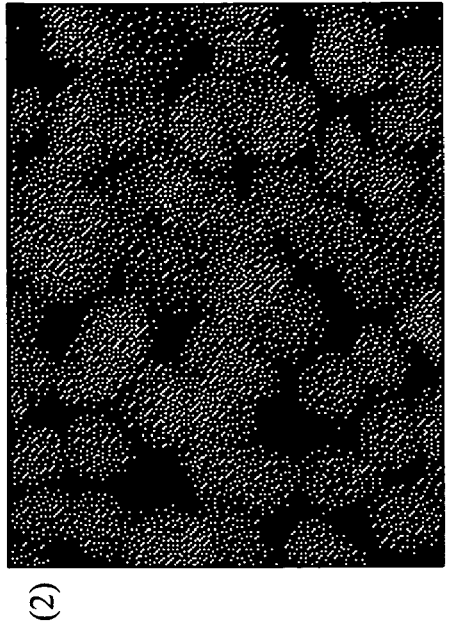
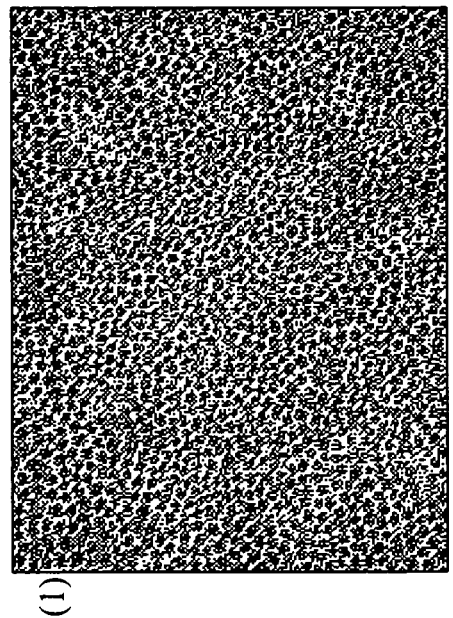
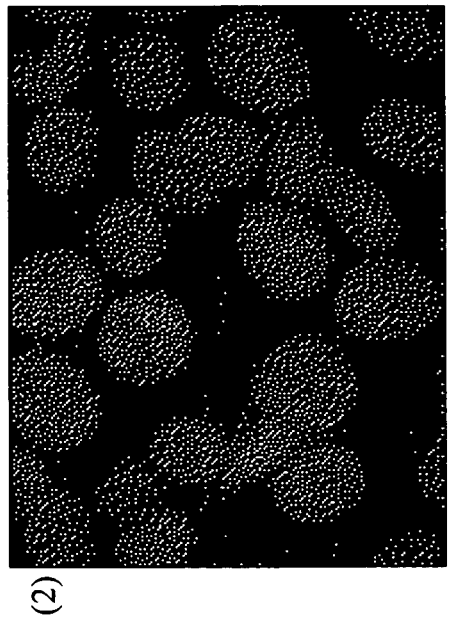
(A) Comparative example 1
(B) Example 2

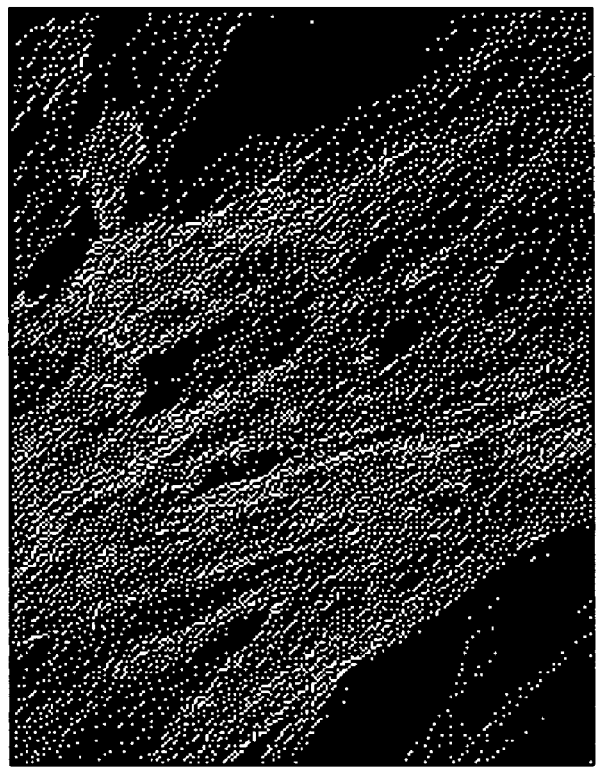
FIG.8

METHOD OF PRODUCING THREE-DIMENSIONAL TISSUE AND METHOD OF PRODUCING EXTRACELLULAR MATRIX USED IN THE SAME

The patent or application file contains at least one drawing executed in color. Copies of this patent or patent application publication with color drawing(s) will be provided by the Office upon request and payment of the necessary fee.

BACKGROUND OF THE INVENTION

1. Field of the Invention

The present invention relates to a method of producing a three-dimensional tissue in which cell layers are laminated and also to a method of producing an extracellular matrix.

The present disclosure relates to subject matter contained in priority Japanese Application No. 2006-56836, filed on Mar. 2, 2006, which is herein expressly incorporated by reference in its entirety.

2. Description of Related Art

In recent years, regenerative medicine has been attracting great attention. Regenerative medicine has become feasible and actually is in the stage of clinical application with regard to regeneration of tissues with a relatively simple structure, such as bone, cartilage, and skin. However, organs such as kidney and liver have a complex three-dimensional tissue structure composed of many types of cells, and hence, unlike the case of skin or the like, it is difficult to construct the tissues of such organs merely by cell culture. Accordingly, regenerative medicine with regard to regeneration of tissues of such organs still is in the stage of fundamental research. In particular, when cells are cultured artificially, they proliferate two-dimensionally (i.e., in the plane direction) but hardly proliferate three-dimensionally (i.e., in the height direction), which makes it difficult to realize three-dimensional tissue construction with cells merely by cell culture.

Thus, at present, as a method of constructing a tissue with cells, methods of achieving three-dimensional tissue construction by laminating cell sheets each composed of cells having proliferated two-dimensionally have been reported, for example (see JP 2004-261532 A, JP 2004-261533 A, and JP 2005-608 A, for example). For example, according to the method disclosed in JP 2004-261532 A, cells are first cultured on a support coated with a temperature-responsive polymer to induce two-dimensional cell proliferation, thereby forming a single cell layer. Subsequently, the thus-formed cell layer is adhered to a carrier and then the cell layer is separated from the support together with the carrier. Thus, a cell sheet is provided. By laminating a plurality of the thus-obtained cell sheets, three-dimensional tissue construction with the cells is achieved. Furthermore, according to the method disclosed in JP 2004-261533 A or JP 2005-608 A, a fibrin gel layer is formed on a support, and two-dimensional cell proliferation is induced on the fibrin gel layer. Thereafter, the laminate of the fibrin gel layer and the cell layer is separated from the support, thus providing a cell sheet. By laminating a plurality of the thus-obtained cell sheets, three-dimensional tissue construction with the cells is achieved.

However, since the cell layer itself has a very low mechanical strength, it is difficult to separate the cell layer from the support together with the carrier or the fibrin gel layer without losing the shape of the cell layer resulting from the culture on the support. Due to this, in the latter method, the fibrin gel layer with a sufficient mechanical strength is used to facilitate the separation of the fibrin gel layer on which the cell layer is formed. However, in the case where the mechanical strength of the fibrin gel layer is improved by increasing its thickness, there arises a problem in that the thick fibrin gel layer intervenes between the cell layers. When the thick fibrin gel layer intervenes between the cell layers as described above, a time lag or variation may be caused in signal transduction between the respective cell layers because the passage of liquid factors is affected by the diffusion in the gel, for example. Moreover, the intervention of the thick fibrin gel layer may bring about the risk that, for example, after the laminate of the cell sheets has been grafted in a living body, the vascular invasion, which is very important in supplying nutrients and enzymes to the cells inside the laminate, is inhibited by the fibrin gel layer, which may lead to necrosis of the cell layers included in the laminate.

Furthermore, the methods that require separating the cell sheet or laminating the plurality of cell sheets as described above also have a problem in that construction of tissues having a complex shape is difficult. That is, when a tissue to be constructed has a complex shape, the planar shape of a cell sheet to be used also becomes complex. However, separating the cell sheet with high reproducibility while maintaining such a complex planar shape itself is very difficult. Laminating the cell sheets first and then cutting the resultant laminate into a desired shape also can be considered. This, however, still poses a problem because there is a limit on the shape that can be achieve by cutting. In the case where a tissue to be constructed specifically is a tissue with a hollow shape, such as a blood vessel, for example, one may consider laminating the cell sheets and then forming the resultant laminate into a tubular shape by rolling the laminate and adhering its end portions with some means, for example. However, such a technique is very complicated and thus is not practical. Other than the above, various attempts have been made on the construction of three-dimensional tissues. However, there have been problems in that, for example, tissue construction using different types of cells, tissue construction into a desired size, etc. are difficult (see JP 2005-278608 A; Yamada N, Okano Y, Sakai H, Karikusa F, Sawasaki Y, Sakurai Y, Macromol Chem Rapid Commun. 11, 571-576, 1990; Takei, R., Suzuki, D., Hoshiba, T., Nagaoka, M., Seo, S. J., Cho, C. S., Akaike, T., Role of E-cadherin Molecules in Spheroid Formation of Hepatocytes Adhered on Galactose-Carrying Polymer as an Artificial Asialoglycoprotein Model. Biotechnology Letters (2005), 27 (16), 1149-1156; and J. M. Jessup 1, T. J. Goodwin 2, G. Spaulding, Prospects for use of microgravity-substrate d bioreactors to study three-dimensional host-tumor interactions in human neoplasia. Journal of Cellular Biochemistry (1993), 51, 290-300, for example).

SUMMARY OF THE INVENTION

Therefore, with the foregoing in mind, it is an object of the present invention to provide a novel method of producing a three-dimensional tissue by which cell lamination can be carried out easily and to provide a method of producing an extracellular matrix used in the method.

In order to achieve the above object, the present invention provides a method of producing a three-dimensional tissue by cell lamination, including the steps of: (A) forming a cell layer on a substrate; (B) bringing the cell layer formed on the substrate into contact with a solution containing a first substance and a solution containing a second substance alternately, thus forming, on the cell layer, an extracellular matrix (hereinafter referred to simply as an "ECM") in which the first substance and the second substance are laminated alternately; and (C) culturing a cell on the ECM to form a further cell layer. In this method, a combination of the first substance and the second substance is (a) a combination of a protein or polymer having an RGD sequence and a protein or polymer that interacts with the protein or polymer having the RGD sequence or (b) a combination of a protein or polymer that is positively charged and a protein or polymer that is negatively charged.

The present invention also provides a method of producing an ECM for adhering cell layers, including the step of: bringing a cell layer into contact with a solution containing a first substance and a solution containing a second substance alternately, thus forming, on the cell layer, a thin film in which the first substance and the second substance are laminated alternately as an ECM. In this method, a combination of the first substance and the second substance is (a) a combination of a protein or polymer having an RGD sequence and a protein or polymer that interacts with the protein or polymer having the RGD sequence or (b) a combination of a protein or polymer that is positively charged and a protein or polymer that is negatively charged.

According to the ECM production method of the present invention, a nanoscale-thick ECM for adhering cell layers can be produced merely by bringing a cell layer into contact with a first substance-containing solution and a second substance-containing solution alternately. Thus, according to the three-dimensional tissue production method of the present invention that uses this ECM production method, merely by repeating the step of forming a cell layer and the step of bringing the cell layer into contact with a first substance-containing solution and a second substance-containing solution alternately, it is possible to laminate a plurality of cell layers successively with a nanoscale-thick ECM intervening between each pair of the adjacent cell layers. Thus, unlike the conventional methods, the method according to the present invention does not require separating a single cell sheet, laminating a plurality of separated cell sheets, etc., so that the three-dimensional tissue can be produced with excellent reproducibility and efficiency in a very simple manner. Therefore, the three-dimensional tissue production method according to the present invention is particularly suitable for reconstruction of tissues having a complex three-dimensional structure and thus is a very useful technique in the field of regenerative medicine.

BRIEF DESCRIPTION OF THE DRAWINGS

FIG. 4 shows micrographs of the three-dimensional tissue obtained in the above example and a three-dimensional tissue obtained in a comparative example. In FIG. 4, the micrographs of the group (A) show the result obtained in Comparative Example 1 and the micrographs of the group (B) show the result obtained in Example 2. In each of the groups (A) and (B), the micrograph (1) is an image as viewed through a phase-contrast microscope and the micrograph (2) is an image as viewed through a confocal fluorescence microscope.

In FIG. 5, the micrograph (A) shows the X-Y plane of the three-dimensional tissue, the micrograph (B) shows the X-Z plane of the three-dimensional tissue, and the micrograph (C) shows the Y-Z plane of the three-dimensional tissue.

In FIG. 7, the SEM image (A) shows a surface of the three-dimensional tissue and the SEM image (B) shows a cross section of the three-dimensional tissue.

FIG. 8 shows confocal micrographs of a three-dimensional tissue obtained in still another example of the present invention. In FIG. 8, the micrographs (A) and (B) both show the result obtained in Example 4.

In FIG. 9, the micrograph (A) shows an image of a first cell layer, the micrograph (B) shows an image of a second cell layer, the micrograph (C) shows an image of a third cell layer, and the micrograph (D) shows an image of a fourth cell layer.

DETAILED DESCRIPTION OF THE INVENTION

Figure 1:
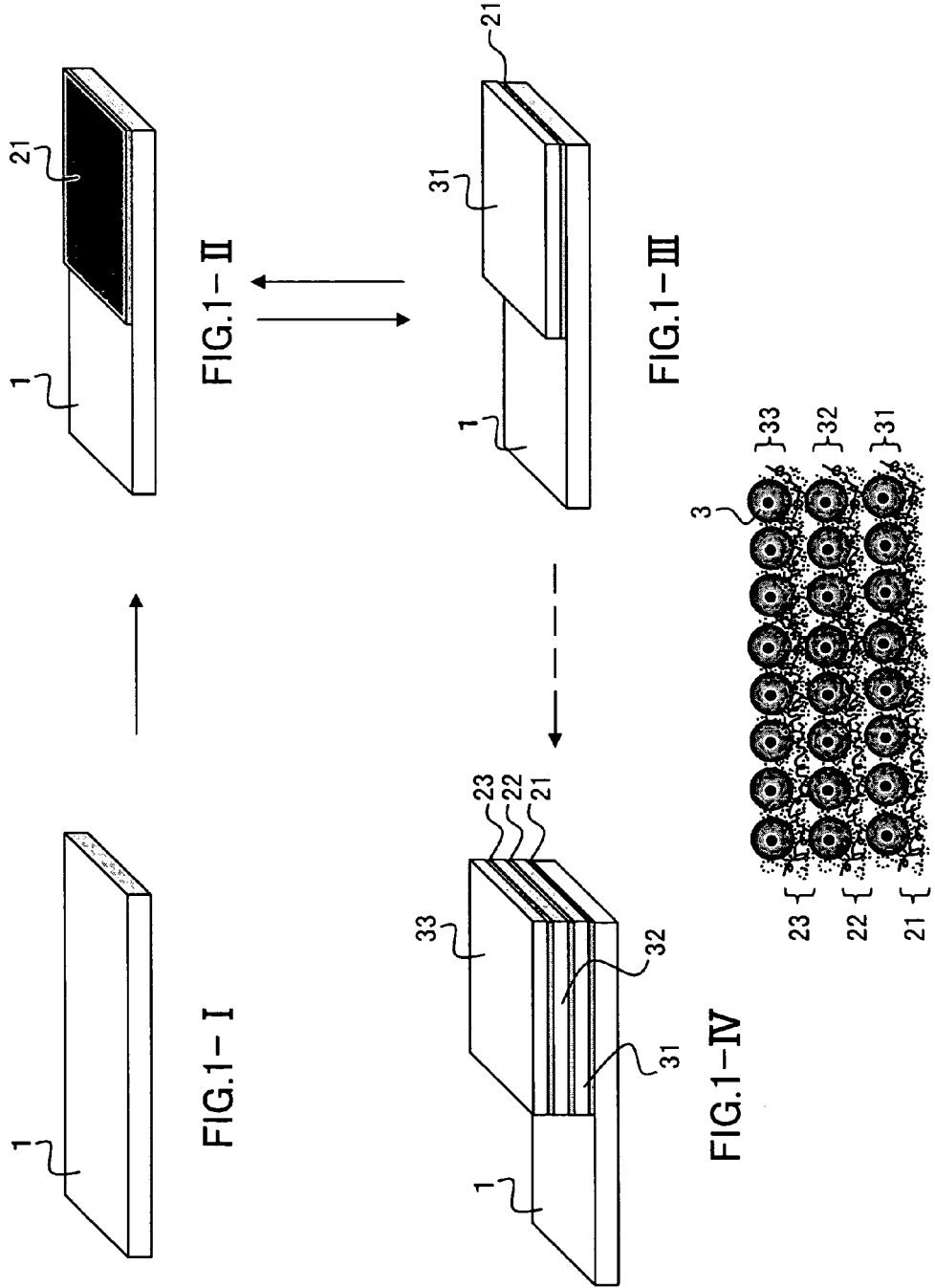
FIGS. 1-I to 1-IV' are schematic views illustrating an example of major steps included in a three-dimensional tissue production method according to the present invention.

In the three-dimensional tissue production method and the ECM production method according to the present invention, the combination of the first substance and the second substance can be (a) a combination of a protein or polymer having an RGD sequence and a protein or polymer that interacts with the protein or polymer having the RGD sequence or (b) a combination of a protein or polymer that is positively charged and a protein or polymer that is negatively charged, as described above. In the present invention, the second substance "interacts" with the first substance means that, for example, the second substance approaches the first substance to the extent that bonding, adhesion, adsorption, or electron transfer can occur chemically or physically between the first substance and the second substance through electrostatic interaction, hydrophobic interaction, hydrogen bonding, charge transfer interaction, formation of a covalent bond, specific interaction between proteins, van der Waals force, or the like.

First Substance Having RGD Sequence

The RGD sequence refers to a generally known "Arg-Gly-Asp" sequence. In the present invention, a substance "having a RGD sequence" may be a substance that has the RGD sequence by nature or a substance to which the RGD sequence is bonded chemically. It is preferable that the first substance is biodegradable.

Examples of the protein having the RGD sequence include conventionally known adhesive proteins such as fibronectin, vitronectin, laminin, cadherin, and collagen. Also, it is possible to use a water-soluble protein having the RGD sequence, examples of which include collagen, gelatin, albumin, globulin, proteoglycan, enzymes, antibodies, etc. to which the RGD sequence is bonded.

The polymer having the RGD sequence may be, for instance, a naturally-occurring polymer or a synthetic polymer. The naturally-occurring polymer is not particularly limited as long as it has the RGD sequence, and examples thereof include water-soluble polypeptides, low molecular weight peptides, polyamino acids such as polylysine, polyester, sugars such as chitin and chitosan, polyurethane, polycarbonate, polyamide, and copolymers thereof. Other specific examples of the first substance are shown in Table 1 below, but the first substance is by no means limited thereto.

TABLE 1

| | Characteristics | Specific example |
|---|---|---|
| Water-soluble polypeptide | Molecular weight: at least 110000 | Polypeptide containing thirteen RGDA sequences in folded-back portion of (Gly-Ala-Gly-Ala-Ser)$_9$ sequence PRONECTIN (trade name, Sanyo Chemical Industries, Ltd.) |
| Low molecular weight peptide | Number of amino acid residues: at least 20 | Peptide (EAK16RGDS in which peptide with (Ala-Glu-Ala-Gul-Ala-Lys-Ala-Lys)$_2$ sequence (EAK16 peptide) is introduced into N-terminal of RGDS Reference document: Biomaterial, 22, 219-225 (2004), Japanese Society for Biomaterials |
| Poly-amino acid | Molecular weight: 2 kDa to 3.4 kDa | Polylysine obtained by grafting RGD and PEG (RGD-grafted PLL-graft-PEG) Reference document: Biotechnology and Bioengineering, 82, 784-790 (2003) |
| Sugar | Molecular weight: at least 2000 | RGD-bonded schizophyllan, curdlan, etc. Reference document: JP 2004-261024 A |
| Co-polymer | Type of monomer: (RGD), PEG, PLA, PGA: 3 (4) | RGD-grafted-PEG-b-PLA-b-PGA Reference document: Biomacromolecules, 7, 590-596 (2006) |

The synthetic polymer is not particularly limited as long as it has the RGD sequence. For example, the synthetic polymer can be a polymer or a copolymer. There is no particular limitation on the polymerization form of the polymer or the copolymer, and they may have a linear, graft, comb, dendritic, or star structure, for instance. Specific examples of the synthetic polymer include polyacrylic acid, polymethacrylic acid, polyethylene glycol-grafted-polyacrylic acid, poly(N-isopropylacrylamide-co-polyacrylic acid), polyamideamine dendrimer, polyethylene oxide, poly(ε-caprolactam), polyacrylamide, and poly(methyl methacrylate-γ-polymethacrylate oxyethylene).

Second Substance that Interacts with First Substance Having RGD Sequence

The second substance is not particularly limited as long as it can interact with the first substance so that both the substances can approach each other to the extent that, for example, bonding, adhesion, adsorption, or electron transfer can occur between these substances. As described above, a protein that interacts with the first substance can be used as the second substance. The protein is not particularly limited, and can be, for instance, a water-soluble protein, specific examples of which include collagen, gelatin, proteoglycan, integrin, enzymes, and antibodies. It is preferable that the second substance is biodegradable.

As the second substance, it is also possible to use a naturally-occurring polymer or synthetic polymer that can interact with the first substance, as described above. The naturally-occurring polymer is not particularly limited, and examples thereof include water-soluble polypeptides, low molecular weight peptides, polyamino acids, polyester, sugars such as heparin and heparan sulfate, polyurethane, polyamide, polycarbonate, and copolymers thereof. Other specific examples of the second substance are shown in Table 2 below, but the second substance is by no means limited thereto.

TABLE 2

| | Characteristics | Specific example |
|---|---|---|
| Water-soluble polypeptide | | Poly (VGVAPG) |
| Low molecular weight peptide | Number of amino acid residues: 6 | VGVAPG |
| Polyamino acid | | polylysine |
| Sugar | | heparin heparan sulfate |
| Copolymer | Type of monomer: PEG, PLA, PGA | PGD-grafted-PEG-b-PLA-b-PGA |

The synthetic polymer is not particularly limited, and can be, for instance, a polymer or a copolymer. The polymer or the copolymer may have various polymerization forms, and they may have a linear, graft, comb, dendritic, or star structure, for instance. Specific examples of the synthetic polymer include polyacrylic acid, polymethacrylic acid, polyethylene glycol-grafted-polyacrylic acid, poly(N-isopropylacrylamide-co-polyacrylic acid), polyamideamine dendrimer, polyethylene oxide, poly(ε-caprolactam), polyacrylamide, and poly(methyl methacrylate-γ-polymethacrylate oxyethylene).

The combination of the above-described first substance and second substance is not particularly limited as long as it is a combination of different substances that interact with each other. Examples of the combination of the first substance and the second substance include combinations of: fibronectin and gelatin; laminin and gelatin; vitronectin and gelatin; fibronectin and dextran sulfate; fibronectin and heparin; elastin and polylysine; fibronectin and collagen; laminin and collagen; vitronectin and collagen; and RGD-bonded collagen or RGD-bonded gelatin and collagen or gelatin. Among these, the combination of fibronectin and gelatin and the combination of laminin and gelatin are preferable, and the combination of fibronectin and gelatin is more preferable. Note here that it is possible to use one type or two or more types of each of the first substance and the second substance as long as they interact with each other.

Positively Charged First Substance

The positively charged protein preferably is, for instance, a water-soluble protein, examples of which include basic collagen, basic gelatin, lysozyme, cytochrome c, peroxidase, and myoglobin.

Furthermore, the positively charged polymer can be, for instance, a naturally-occurring polymer or a synthetic polymer as long as it is positively charged. The naturally-occurring polymer is not particularly limited, and examples thereof include water-soluble polypeptides, low molecular weight peptides, polyamino acids, polyester, sugars, polyurethane, polyamide, polycarbonate, and copolymers thereof.

The synthetic polymer is not particularly limited, and can be, for instance, a polymer or a copolymer. The polymer or the copolymer may have various polymerization forms, and they may have a linear, graft, comb, dendritic, or star structure, for instance. Specific examples of the synthetic polymer include chitin, chitosan, poly($\alpha$-lysine), poly($\epsilon$-lysine), polyarginine, polyhistidine, polydiallyldimethylammonium chloride, polyallylamine hydrochloride, polyethyleneimine, polyvinylamine, and polyamideamine dendrimer.

Negatively Charged Second Substance

The negatively charged protein preferably is, for instance, a water-soluble protein, examples of which include acidic collagen, acidic gelatin, albumin, globulin, catalase, $\beta$-lactoglobulin, thyroglobulin, $\alpha$-lactalbumin, and ovalbumin.

Furthermore, the negatively charged polymer can be, for instance, a naturally-occurring polymer or a synthetic polymer as long as it is negatively charged. The naturally-occurring polymer is not particularly limited, and examples thereof include water-soluble polypeptides, low molecular weight peptides, polyamino acids, polyester, sugars, polyurethane, polyamide, polycarbonate, and copolymers thereof.

The synthetic polymer is not particularly limited, and can be, for instance, a polymer or a copolymer. The polymer or the copolymer may have various polymerization forms, and they may have a linear, graft, comb, dendritic, or star structure, for instance. Specific examples of the synthetic polymer include polyester, polyacrylic acid, polymethacrylic acid, polystyrene sulfonate, polyacrylamidomethylpropane sulfonic acid, and terminal-carboxylated polyethylene glycol.

Examples of the combination of the positively charged first substance and the negatively charged second substance include combinations of chitosan and dextran sulfate; polyallylamine hydrochloride and polystyrene sulfonate; polydiallyldimethylammonium chloride and polystyrene sulfonate. Among these, the combination of chitosan and dextran sulfate is preferable. Note here that it is possible to use one type or two or more types of each of the first substance and the second substance as long as they interact with each other.

An example of the three-dimensional tissue production method and the ECM production method according to the present invention will be described with reference to FIGS. 1-I to 1-IV'. FIGS. 1-I to 1-IV' are schematic views illustrating major steps in the three-dimensional tissue production method according to the present invention. It should be noted, however, that the production methods according to the present invention are by no means limited to the illustrative methods given below.

Formation of ECM on Substrate

First, a substrate 1 (FIG. 1-I) is brought into contact with a first substance-containing solution and a second substance-containing solution alternately, thus forming, on the substrate 1, an ECM 21 in which the first substance and the second substance are laminated alternately (FIG. 1-II). Hereinafter, the method of bringing the substrate with two or more types of solutions so as to laminate substances contained in the respective solutions is referred to also as a "Layer-by-Layer (LBL)" method. Hereinafter, the ECM formed on the substrate is referred to as the "first nano-ECM".

The solution with which the substrate is brought into contact first may be either the first substance-containing solution or the second substance-containing solution. The ECM can be formed by repeating the step of bringing the substrate into contact with either one of the solutions and then with the other solution. According to such an LBL method, it is possible to form an ECM with a nanoscale thickness as will be described later.

Furthermore, in the process of forming the ECM on the substrate, the solution with which the substrate is brought into contact last may be either the first substance-containing solution or the second substance-containing solution, but preferably is the first substance-containing solution because fibronectin, laminin, or the like exhibits excellent adhesion to cells. In this case, an uppermost layer of the nano-ECM formed on the substrate would be a first substance layer (e.g., a fibronectin layer, a laminin layer, or the like).

The number of times the substrate is brought into contact with both the solutions is not particularly limited, and can be determined as appropriate depending on the desired thickness of the nano-ECM to be formed. That is, the step of bringing the substrate into contact with both the solutions may be repeated until the nano-ECM having the desired thickness is obtained. The thickness of the nano-ECM also can be adjusted by, for example, adjusting the first substance concentration, the second substance concentration, and/or the salt concentration in the solutions. However, it is easy to adjust the thickness of the nano-ECM by adjusting the number of times the substrate is brought into contact with both the solutions. That is, for example, a relatively thick nano-ECM can be obtained by increasing the number of times the substrate is brought into contact with both the solutions, whereas a relatively thin nano-ECM can be obtained by decreasing the number of times the substrate is brought into contact with both the solutions.

The concentration of the first substance in the first substance-containing solution is not particularly limited, and can be, for example, 0.0001 to 1 wt %, preferably 0.01 to 0.5 wt %, and more preferably 0.02 to 0.1 wt %. Specifically, in the case where the first substance is fibronectin, the concentration thereof is, for example, 0.0001 to 1 wt %, preferably 0.01 to 0.5 wt %, and more preferably 0.02 to 0.1 wt %. In the case where the first substance is laminin, the concentration thereof is, for example, 0.0001 to 1 wt %, preferably 0.01 to 0.5 wt %, and more preferably 0.02 to 0.1 wt %. Also, the concentration of the second substance in the second substance-containing solution is not particularly limited, and can be, for example, 0.0001 to 1 wt %, preferably 0.01 to 0.5 wt %, and more preferably 0.02 to 0.1 wt %. Specifically, in the case where the second substance is gelatin, the concentration thereof is, for example, 0.0001 to 1 wt %, preferably 0.01 to 0.5 wt %, and more preferably 0.02 to 0.1 wt %.

The solvent used in each of the solutions is not particularly limited, and can be an aqueous solvent such as water or a buffer. Examples of the buffer include Tris buffers such as Tris-HCl buffer, phosphate buffer, HEPES buffer, citric acid-phosphate buffer, glycylglycine-sodium hydroxide buffer, Britton-Robinson buffer, and GTA buffer. The pH of the buffer is not particularly limited, and can be, for example, 3 to 11, preferably 6 to 8, and more preferably 7.2 to 7.4. The solution can be prepared by, for example, dissolving or dispersing the first substance or the second substance in the solvent.

As already described above, it is also possible to adjust the thickness of the nano-ECM to be formed by adjusting the concentration of the first substance and the concentration of the second substance in the respective solutions. That is, the thickness of a layer formed each time the substrate is brought into contact with the first substance-containing solution or the second substance-containing solution can be adjusted by adjusting the concentration of the first substance or the second substance in the solution. Specifically, a relatively thick layer can be formed each time the substrate is brought into contact with the first substance-containing solution or the second substance-containing solution by making the concentration of the first substance or the second substance in the solution relatively high, whereas a relatively thin layer can be formed each time the substrate is brought into contact with the first substance-containing solution or the second substance-containing solution by making the concentration of the first substance or the second substance in the solution relatively low.

The solutions further may contain a salt, examples of which include sodium chloride, calcium chloride, sodium hydrogen carbonate, sodium acetate, sodium citrate, potassium chloride, sodium hydrogen phosphate, magnesium sulfate, and sodium succinate. Note here that one or both of the solutions may contain the salt. The concentration of the salt in the solution is not particularly limited, and can be, for example, $1\times10^{-6}$ to 2 M, preferably $1\times10^{-4}$ to 1 M, and more preferably $1\times10^{-4}$ to 0.05 M. The solution may contain one type or two or more types of salts.

The thickness of the nano-ECM to be formed can be adjusted by adjusting the content of the salt in the solution, for example. That is, the thickness of a layer formed each time the substrate is brought into contact with the first substance-containing solution or the second substance-containing solution can be adjusted by adjusting the concentration of the salt in the solution. Specifically, a relatively thick layer can be formed each time the substrate is brought into contact with the first substance-containing solution or the second substance-containing solution by making the concentration of the salt in the solution relatively high, whereas a relatively thin layer can be formed each time the substrate is brought into contact with the first substance-containing solution or the second substance-containing solution by making the concentration of the salt in the solution relatively low.

The first substance-containing solution and the second substance-containing solution further may contain a cell growth factor, cytokine, chemokine, hormone, or biologically active peptide. By adding the growth factor etc. to the solution, it becomes possible to adjust, for instance, the speed or extent of cell proliferation during the formation of the cell layer.

Also, the first substance-containing solution and the second substance-containing solution further may contain a pharmaceutical composition such as a therapeutic agent for treating a disease, a prophylactic agent for preventing a disease, an inhibitor for inhibiting a disease, an antibacterial agent, or an antiinflammatory agent. Because a three-dimensional tissue produced by using such solutions contains the above-described pharmaceutical composition, it is also possible to treat or prevent the disease by grafting the three-dimensional tissue in the body of a human, a mammal other than a human, or any other animal, for example.

The method of bringing the substrate into contact with the respective solutions is not particularly limited. Examples of the method include: dipping the substrate in the respective solutions; and dripping or spraying the respective solutions on the substrate. However, in terms of simplicity in operation, the method of dipping the substrate is preferable. The conditions under which the substrate is brought into contact with the solutions are not particularly limited, and can be determined as appropriate depending on the contact method, the concentration of the substance in the solution to be used, etc. Specifically, the contact time is not particularly limited, and can be, for example, 1 to 1440 minutes, preferably 5 to 60 minutes, and more preferably 10 to 15 minutes, and the contact temperature is not particularly limited, and can be, for example, 4° C. to 60° C., preferably 20° C. to 40° C., and more preferably 30° C. to 37° C.

After the substrate has contacted with either one of the solutions, the substrate may be brought into contact with the other solution as it is. Alternatively, the substrate may be brought into contact with the other solution after it has been dried by air drying or the like, for example. Also, after the substrate has contacted with one of the solutions, the substrate may be brought into contact with the other solution after the surface thereof has been washed with a solvent. The solvent used for washing the substrate surface is not particularly limited, and examples thereof include aqueous solvents such as water and the above-described buffers.

There is no limitation on the type of the substrate. For example, the shape, form, or material thereof is not particularly limited, and it is possible to use any conventionally known substrates. The material of the substrate is not particularly limited, and examples thereof include glass, various polymers, filter papers, metals, and hydrogels. The form of the substrate also is not particularly limited, and the substrate can be, for instance, a non-porous substrate, a porous substrate, a substrate formed of fiber, or a substrate formed of a fabric such as a woven fabric or a nonwoven fabric. Furthermore, the ECM in the present invention can be formed on surfaces of hydrogels, medical materials, artificial organs, phospholipid films such as cell membranes, for example.

In the above-described manner, the nanoscale-thick ECM in which the first substance and the second substance are laminated alternately is formed on the surface of the substrate. The thickness of the nano-ECM to be formed by bringing the substrate into contact with each of the solutions is not particularly limited as long as it is a nanoscale thickness, and can be, for instance, 1 to 1000 nm, preferably 1 to 300 nm, and more preferably 5 to 100 nm.

Formation of Cell Layer: Step (A)

Subsequently, cells are cultured on a surface of the nano-ECM 21 formed on substrate 1, thus forming a cell layer 31 (FIG. 1-III). By culturing the cells on the nano-ECM as described above, the cells proliferate two-dimensionally (i.e., in the plane direction) to form the single cell layer, resulting in the state where the cells adhere to the surface of the nano-ECM. When forming a first cell layer on the substrate, the cell layer may be formed on the substrate directly without forming the above-described nano-ECM.

The type of the cells is not particularly limited, and examples thereof include adhesive cells such as hepatocytes, vascular endothelial cells, fibroblasts, epidermic cells, epithelial cells, mammary glandular cells, myocytes, neurocytes, tissue stem cells, embryonic stem cells, bone cells, and immunocytes. Note here that one type of cells may be cultured, or two or more types of cells may be cocultured. When using two or more types of cells, cell layers each composed of the same type of cells may be laminated with an ECM intervening between each pair of the adjacent cell layers, or alternatively, a single cell layer composed of a plurality of types of cells may be formed, for example.

The conditions of the cell culture are not particularly limited, and can be determined as appropriate depending on the type of cells to be cultured. In general, the cell culture is carried out at the culture temperature of, for instance, 4° C. to 60° C., preferably 20° C. to 40° C., and more preferably 30° C. to 37° C., and the culture period of, for instance, 1 to 168 hours, preferably 3 to 24 hours, and more preferably 3 to 12 hours. The culture medium used for the cell culture is not particularly limited, and can be determined as appropriate depending on the type of cells. Examples of the culture medium include Eagle's minimum essential medium (Eagle's MEM), Dulbecco's modified Eagle's medium (D-MEM), modified Eagle medium, minimum essential medium, RDMI, Glutamax medium, and serum-free medium. The density of the cells to be seeded is not particularly limited, and can be, for example, $0.01\times10^4$ to $100\times10^4$ cells/cm$^2$, preferably $1\times10^4$ to $10\times10^4$ cells/cm$^2$.

Formation of Nano-ECM on Cell Layer: Step (B)

The cell layer formed on the substrate is brought into contact with a fibronectin-containing solution and a gelatin-containing solution alternately, thus forming, on the cell layer, a nano-ECM (hereinafter referred to also as a "second nano-ECM") in which fibronectin and gelatin are laminated alternately. Unless otherwise stated, the second nano-ECM may be formed in the same manner as described above.

The solution with which the cell layer is brought into contact first may be either the first substance-containing solution or the second substance-containing solution, but preferably is the first substance-containing solution because fibronectin, laminin, or the like exhibits excellent adhesion to cells. In this case, a lowermost layer of the nano-ECM formed on the cell layer would be a first substance layer (e.g., a fibronectin layer, a laminin layer, or the like). Also, the solution with which the cell layer is brought into contact last may be either the first substance-containing solution or the second substance-containing solution, but preferably is the first substance-containing solution in view of the excellent adhesion to cells as described above. In this case, an uppermost layer of the nano-ECM formed on the cell layer would be a first substance layer.

The number of times the cell layer is brought into contact with both the solutions is not particularly limited, and can be determined as appropriate depending on the desired thickness of the nano-ECM to be formed, as described above. The thickness of the nano-ECM to be formed is not particularly limited as long as it is a nanoscale thickness, and can be, for instance, 1 to 1000 nm, preferably 1 to 100 nm, and more preferably 5 to 100 nm.

Formation of Cell Layer on Nano-ECM: Step (C)

Cells are cultured on the second nano-ECM to form a further cell layer (a second cell layer). In this manner, it is possible to form a three-dimensional tissue in which the two cell layers are laminated with the nano-ECM intervening therebetween. Note here that the cell culture method is the same as that described above.

Layer-by-Layer Assembly of Nano-ECMs and Cell Layers

When laminating three or more cell layers, the step (B) and the step (C) may be repeated so as to laminate a further nano-ECM(s) and a further cell layer(s) alternately on the cell layer.

The number of times the step (B) and the step (C) are performed is not particularly limited, and can be determined as appropriate depending on the desired size (thickness) of the three-dimensional tissue to be formed, the desired number of the cell layers, etc. Specifically, when laminating n layers (n is an integer of 2 or more) is desired, this can be achieved by performing each of the step (B) and the step (C) alternately (n−1) times. In the case where the uppermost layer of the three-dimensional tissue is a cell layer, a nano-ECM further may be formed thereon in the same manner as described above.

The schematic view of FIG. 1-IV shows an example where three cell layers are laminated in the three-dimensional tissue. As shown in FIG. 1-IV, in this three-dimensional tissue, the first nano-ECM 21, the first cell layer 31, the second nano-ECM 22, the second cell layer 32, a third nano-ECM 23, and a third cell layer 33 are laminated on the substrate 1 in this order. This three-dimensional tissue is obtained by, for example, performing the step (A) and then performing the step (B) and the step (C) alternately twice as described above. FIG. 1-IV' schematically shows the structure of the three-dimensional tissue. As shown in FIG. 1-IV', in the three-dimensional tissue, the single cell layers (31, 32, 33) resulting from the two-dimensional proliferation of the cells 3 are laminated on the laminates (21, 22, 23) of the first substance and the second substance, respectively.

Thus, according to the three-dimensional tissue production method according to the present invention, by merely repeating the step of forming a single cell layer and the step of bringing the cell layer into contact with a first substance-containing solution and a second substance-containing solution alternately as described above, it is possible to laminate a plurality of cell layers successively in the height direction (z-axis direction) with a nanoscale-thick ECM intervening between each pair of the adjacent cell layers. Thus, the three-dimensional tissue production method according to the present invention does not require separating a single cell sheet, laminating a plurality of separated cell sheets, etc., so that a three-dimensional tissue can be produced with excellent reproducibility and efficiency in a very simple manner. Moreover, the three-dimensional tissue production method according to the present invention can be carried out with the simple steps as described above, and it allows an ECM(s) and a cell layer(s) to be formed in a desired region. Thus, the method according to the present invention is advantageous in that, for example, the ECM can be formed on a surface with any shape to adhere cells thereto, so that it becomes possible to produce a three-dimensional tissue with a complex shape. For example, in the case of a three-dimensional tissue with a hollow shape, such as a blood vessel, by repeating the step of forming a cell layer and an ECM alternately on a surface of a ring-shaped substrate, the cell layers can be laminated successively in the direction toward the central axis of the ring-shaped substrate. Thus, it is possible to obtain a three-dimensional tissue with a tubular shape (a hollow shape) without performing the steps of adhering the cell layers etc. as in the prior art. That is, tissues with any cross sections (X-Y plane) can be formed by setting a planar region on which an ECM(s) and a cell layer(s) are to be formed. Moreover, for example, it is possible to form an extracellular matrix on an inner surface of an artificial blood vessel by causing a first substance-containing solution and a second substance-containing solution to flow on the inner surface alternately and then adhere cells to the thus-formed extracellular matrix by rotating the artificial blood vessel while causing a cell solution to flow on the extracellular matrix. By repeating the above step, a plurality of cell layers can be formed on the inner surface of a tubular structure such as the artificial blood vessel.

Hereinafter, the present invention will be described more specifically by way of examples and comparative examples. It is to be noted, however, the present invention is by no means limited to the following examples.

EXAMPLE 1

A nanoscale-thick nano-ECM in which fibronectin and gelatin were laminated alternately was produced. The substrate used for the nano-ECM formation was a quartz crystal microbalance (QCM) substrate, and the thickness of the matrix being formed was determined by measuring a frequency shift.

Figure 2:
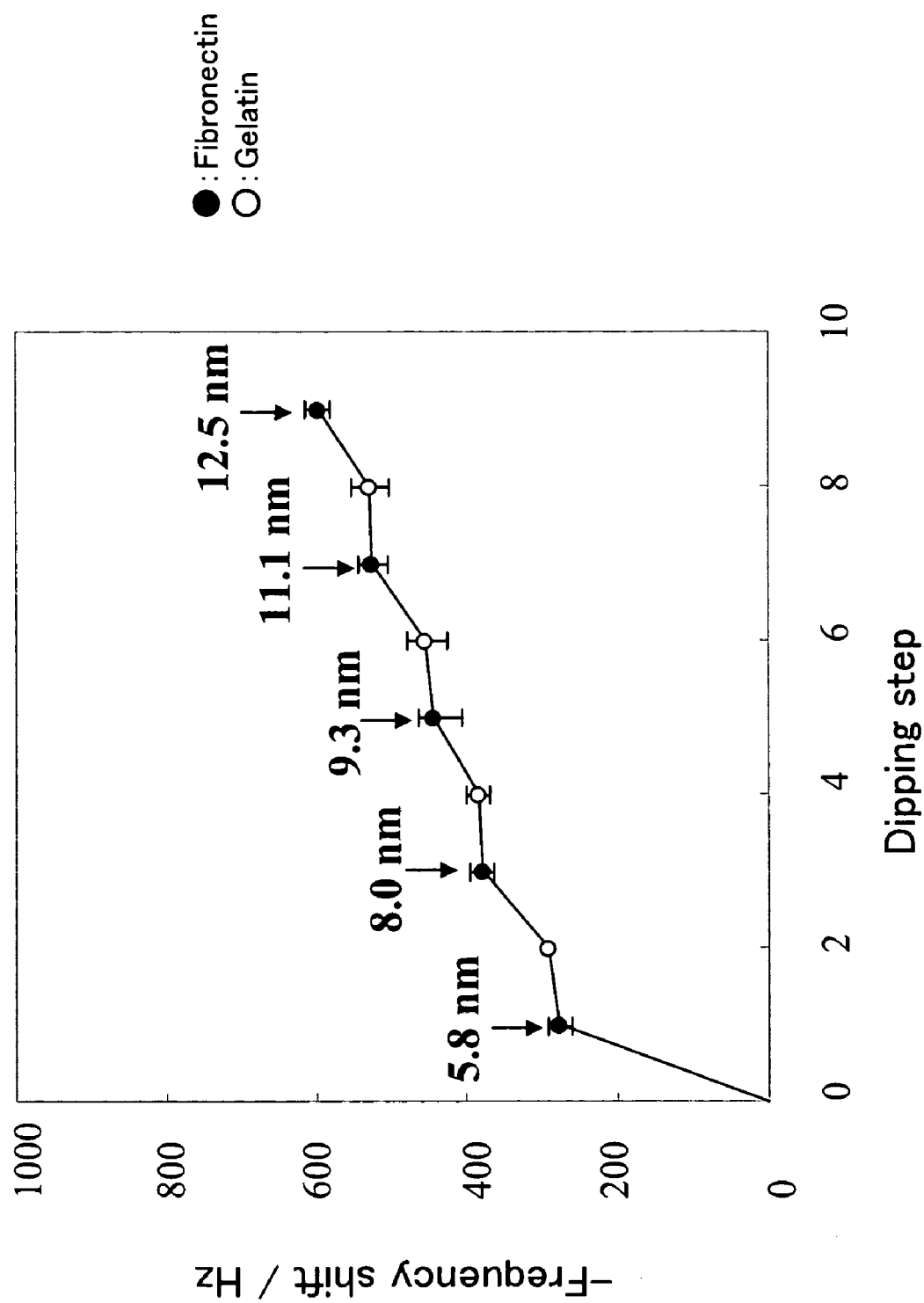
FIG. 2 is a graph showing the relationship between a frequency shift and the number of dipping steps performed in one example of the present invention.

First, the QCM substrate was washed with a piranha solution for 1 minute and then dipped in a 0.5 M Tris buffer containing 0.2 mg/ml (0.02 wt %) fibronectin (pH 7.4, hereinafter the same) at 37° C. for 15 minutes. Subsequently, the substrate was washed with a 1 mM Tris buffer (pH 7.4) and then air-dried, after which the frequency shift was measured. Next, the substrate was dipped in a 0.05M Tris buffer containing 1 mg/ml (0.1 wt %) gelatin (pH 7.4, hereinafter the same) at 37° C. for 15 minutes. Again, the substrate was washed with a 1.0 mM Tris buffer (pH 7.4) and then air-dried, after which the frequency shift was measured. By repeating these steps alternately, nano-ECMs (n=3) were formed on the QCM substrate. The frequency shifts measured in the respective steps are shown in FIG. 2. In FIG. 2, a filled circle indicates the result obtained after the dipping in the fibronectin-containing buffer, and an open circle indicates the result obtained after the dipping in the gelatin-containing buffer. The thickness of the nano-ECM after each step also is shown in FIG. 2.

As shown in FIG. 2, the frequency shift decreased as the steps were repeated, which demonstrates that the nanoscale layers were formed successively on the QCM substrate. Furthermore, the fact that the decrease in the frequency correlated with the number of steps teaches that the thickness of a nano-ECM to be formed can be increased by increasing the number of steps and can be decreased by decreasing the number of steps.

EXAMPLE 2

Nano-ECMs each composed of gelatin and fibronectin were produced to construct a three-dimensional tissue with mouse fibroblasts (L929).

A first nano-ECM was formed on a slide glass (1.5 cm in width×2 cm in length) in the following manner.

The first nano-ECM was formed by dipping the slide glass in the fibronectin-containing buffer and the gelatin-containing buffer. Note here that the seven dipping steps were performed in total with the buffer in which the slide glass was dipped first being the fibronectin-containing buffer. After the slide glass had been dipped in the respective buffers, the slide glass was washed by being dipped in a 50 mM Tris buffer (pH 7.4) for 1 minute. As a result, about 10 nm thick nano-ECM whose lowermost layer and uppermost layer were both fibronectin layers was formed on the slide glass. Note here that dipping of the slide glass in either of the buffers at 37° C. for 15 minutes was regarded as one dipping step. Also note that only an end portion (1.5 cm in width×2.0 cm in length) of the slide glass was dipped in the buffers so that the nano-ECM was formed only on the dipped region.

Next, on the surface (1.5 cm×2.0 cm) of the first nano-ECM, L929 cells (the number of cells: about $1 \times 10^5$) were seeded so that the cell density would be about $3.3 \times 10^4$ cells/cm². After Eagle's MEM containing 10 wt % fetal bovine serum (FBS) was added to the surface of the first nano-ECM, the cells were incubated at 37° C. for 6 hours. As a result, the cells proliferated two-dimensionally on the first nano-ECM to form a single cell layer, whereby the cells that proliferated were adhered to the first nano-ECM.

Subsequently, the slide glass was washed by being dipped in a 50 mM Tris buffer (pH 7.4) for 1 minute, and thereafter, a second nano-ECM further was formed on the cells having proliferated on the first nano-ECM. The second nano-ECM was formed in the same manner as the first nano-ECM, except that the slide glass was dipped in the fibronectin-containing buffer and the gelatin-containing buffer alternately so that the nine dipping steps were performed in total with the buffer in which the slide glass was dipped first being the fibronectin-containing buffer. As a result, the second nano-ECM having a thickness of about 13 nm was formed on the surface of the cells having proliferated on the first nano-ECM.

Subsequently, the cell layer formation and the nano-ECM formation were performed repeatedly in the same manner as described above, thus forming a three-dimensional tissue having a layered structure composed of first nano-ECM/first cell layer/second nano-ECM/second cell layer/third nano-ECM/third cell layer/fourth nano-ECM/fourth cell layer on the slide glass. The third nano-ECM and the fourth nano-ECM were formed in the same manner as the second nano-ECM, and the thicknesses of the third nano-ECM and the fourth nano-ECM were both about 13 nm. Furthermore, as Comparative Example 1, cell culture was carried out in the same manner as in Example 2, except that no nano-ECMs were formed.

Figure 3:
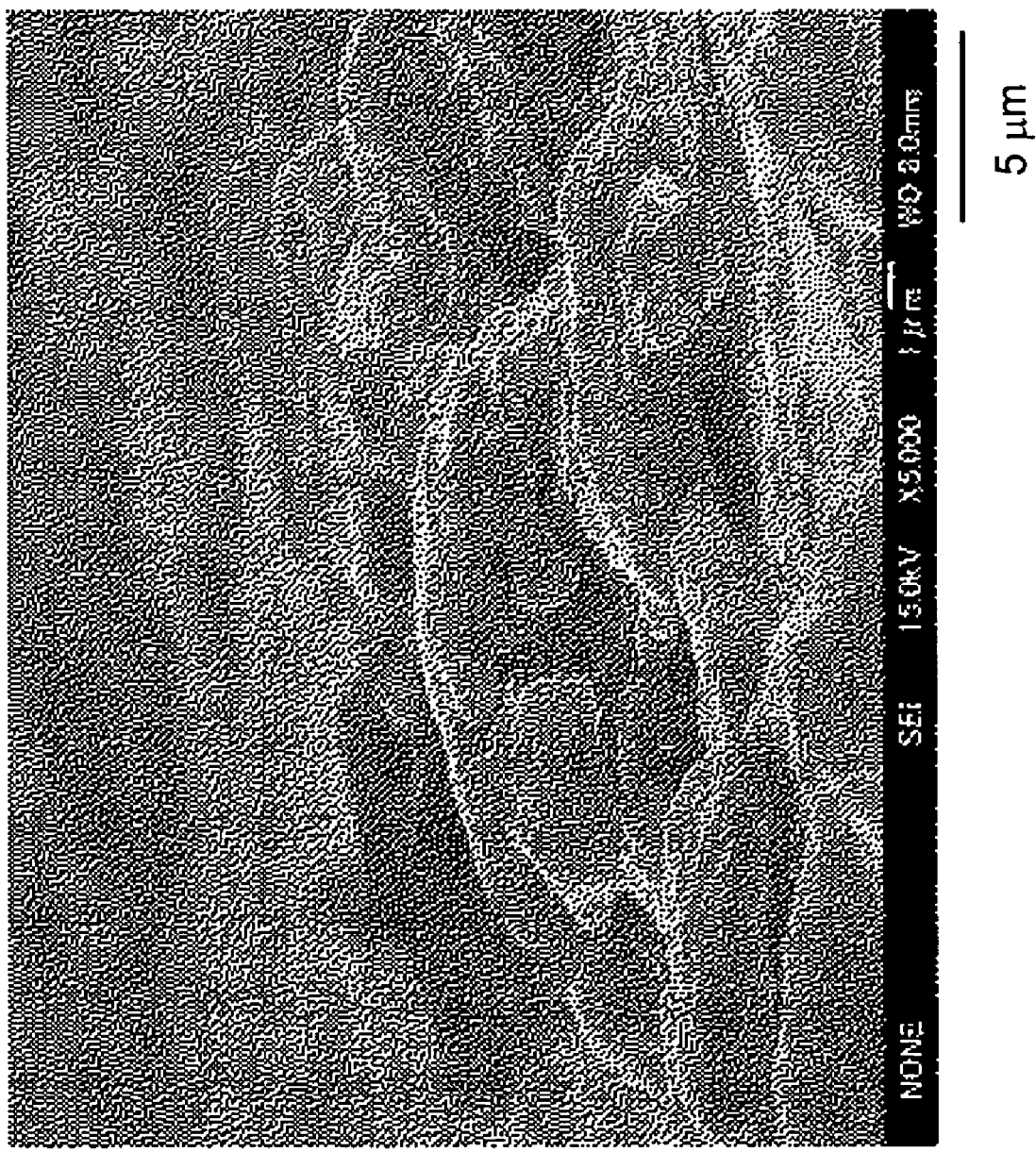
FIG. 3 shows a SEM image showing a three-dimensional tissue obtained in another example of the present invention.

The surface of the three-dimensional tissue obtained in Example 2 was observed with a scanning electron microscope (SEM). The result is shown in the micrograph of FIG. 3. As can be seen from FIG. 3, the cells were laminated in the height direction (the z-axis direction).

Also, the three-dimensional tissue was evaluated using a phase-contrast microscope and a confocal fluorescence microscope. The observation with the confocal fluorescence microscope was carried out after nuclear staining of the three-dimensional tissue with DAPI (4',6-diamidino-2-phenylindole, dihydrochloride). Also, with regard to the three-dimensional tissue obtained in Comparative Example 1, the observation was carried out in the same manner. The results are shown in FIG. 4. In FIG. 4, the micrographs of the group (A) show the result obtained in Comparative Example 1 and the micrographs of the group (B) show the result obtained in Example 2. In each of the groups (A) and (B), the micrograph (1) is an image as viewed through the phase-contrast microscope and the micrograph (2) is an image as viewed through the confocal fluorescence microscope. As a result, it was found that, since no nano-ECMs were formed in Comparative Example 1, the cells proliferated only two-dimensionally and were not laminated in the height direction (the z-axis direction). Accordingly, the cells having proliferated adhered only to the surface of the slide glass, so that only the two-dimensional cell density was improved. In contrast, in Example 2, cell lamination was observed as shown in the phase-contrast micrograph (1) in the group (B) of FIG. 4. In particular, lamination of the stained nuclei in the height direction (the z-axis direction) was observed in the confocal micrograph (2) in the group (B) of FIG. 4, and it was found that the focal lengths in the z-axis direction in the confocal micrograph (2) in the group (B) were different between the adjacent cell layers by about 5 μm.

These results demonstrate that, in Example 2, the cell lamination in the height direction became possible by the formation of the nano-ECMs, thus realizing the construction of the three-dimensional tissue.

EXAMPLE 3

Nano-ECMs each composed of fibronectin and gelatin were produced to laminate mouse fibroblasts (L929) three-dimensionally. The resultant three-dimensional tissue was evaluated using a confocal laser microscope.

Nano-ECMs and cell layers were laminated on a slide glass in the same manner as in Example 2, thus forming a three-dimensional tissue having a layered structure composed of first nano-ECM/first cell layer/second nano-ECM/second cell layer. The thickness of the first nano-ECM was about 13 nm and the thickness of the second nano-ECM was about 13 nm as in Example 2.

Figure 5:
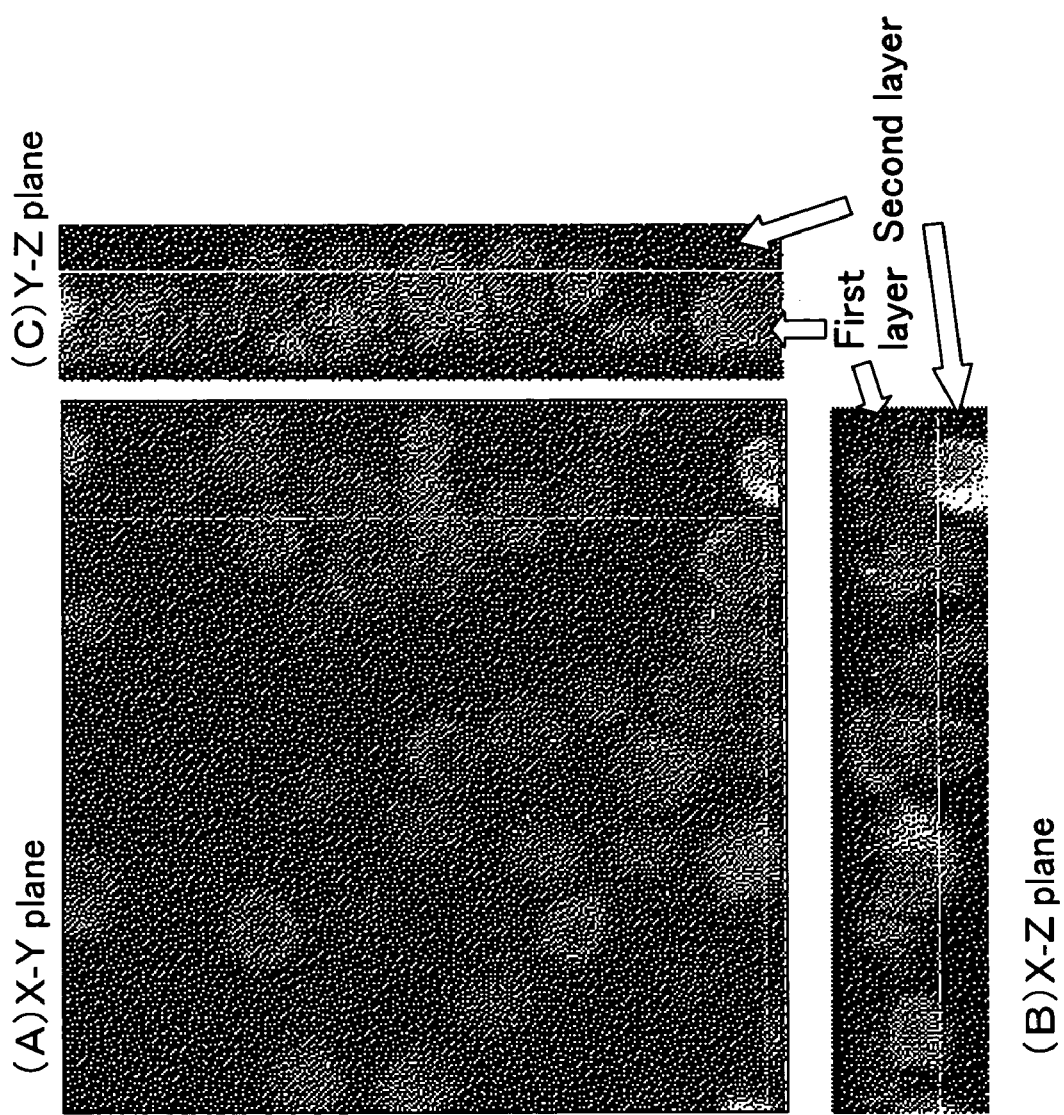
FIG. 5 shows confocal laser micrographs of a three-dimensional tissue in still another example of the present invention.
Figure 6:
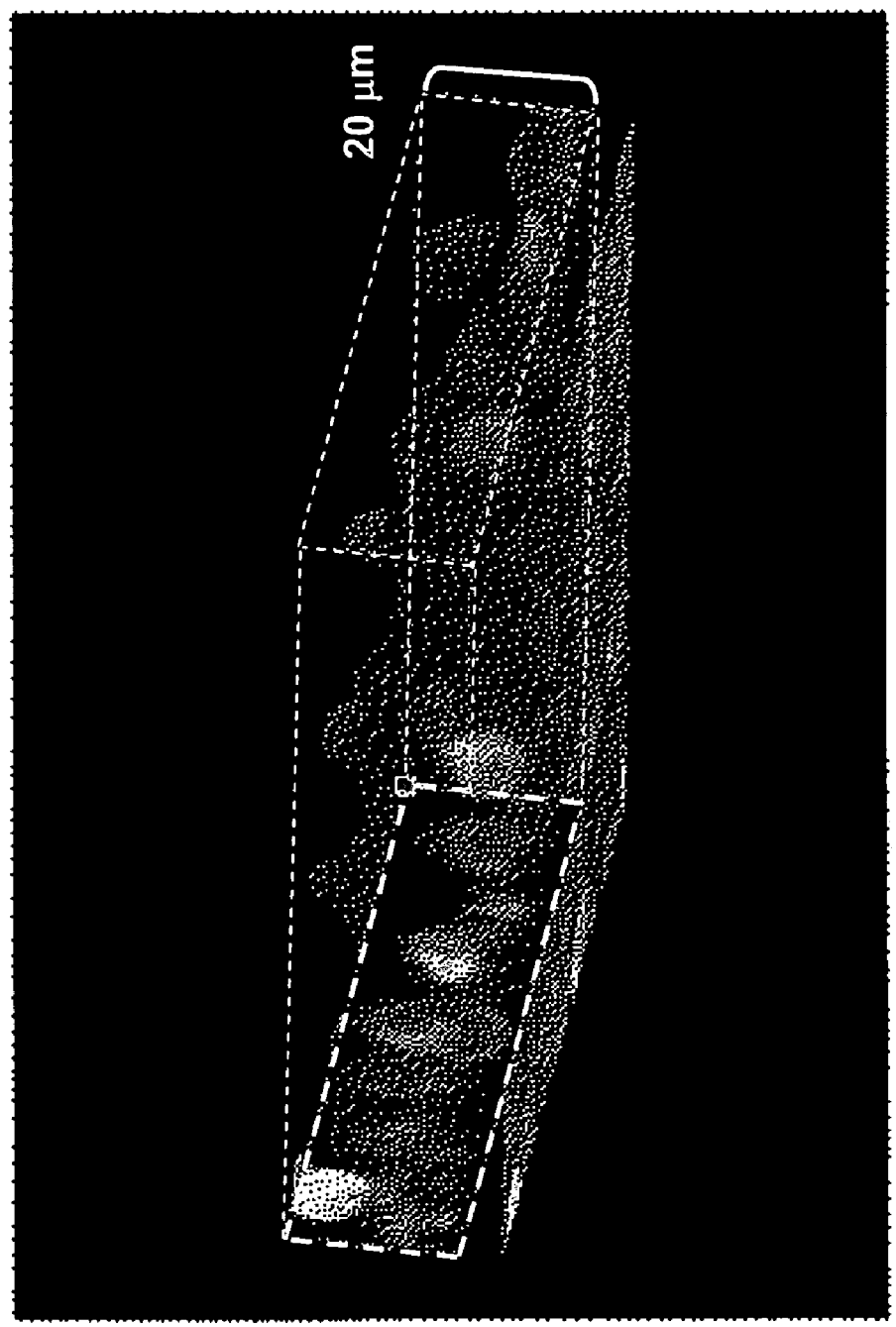
FIG. 6 shows a 3-D image of the three-dimensional tissue obtained in the above example as viewed through a confocal laser microscope.

The three-dimensional structure of the thus-obtained three-dimensional tissue was observed with a confocal laser microscope. The results are shown in FIGS. 5 and 6. In FIG. 5, the micrograph (A) shows the X-Y plane of the three-dimensional tissue, the micrograph (B) shows the X-Z plane of the three-dimensional tissue, and the micrograph (C) shows the Y-Z plane of the three-dimensional tissue. The micrograph (D) shown in FIG. 6 is a 3-D image of the three-dimensional tissue.

As shown in FIGS. 5 and 6, the first cell layer and the second cell layer laminated on the first cell layer were observed. This demonstrates that, in Example 3, the cell lamination in the height direction became possible by the formation of the nano-ECMs.

EXAMPLE 4

Nano-ECMs each composed of gelatin and fibronectin were produced to laminate human umbilical artery smooth muscle cells (UASMCs) three-dimensionally.

A first nano-ECM (thickness: about 13 nm) was formed on a slide glass in the same manner as in Example 2.

Next, on the surface of the first nano-ECM, the UASMCs (the number of cells: about $1 \times 10^5$) were seeded so that the cell density would be about $3.3 \times 10^4$ cells/cm$^2$. Then, the UASMCs were cultured in Eagle's MEM containing 10 wt % FBS at 37° C. for 6 hours. As a result, the cells proliferated two-dimensionally on the first nano-ECM to form a single cell layer, whereby the cells that proliferated were adhered to the first nano-ECM.

Then, a second nano-ECM (thickness: about 13 nm) further was formed on the cells having proliferated on the first nano-ECM in the same manner as in Example 2.

Subsequently, the cell proliferation and the nano-ECM formation were performed repeatedly in the same manner as described above, thus forming a three-dimensional tissue having a layered structure composed of first nano-ECM/first cell layer/second nano-ECM/second cell layer/third nano-ECM/third cell layer on the slide glass. The third nano-ECM was formed in the same manner as the second nano-ECM, and the thickness of the third nano-ECM was about 13 nm.

Figure 7:
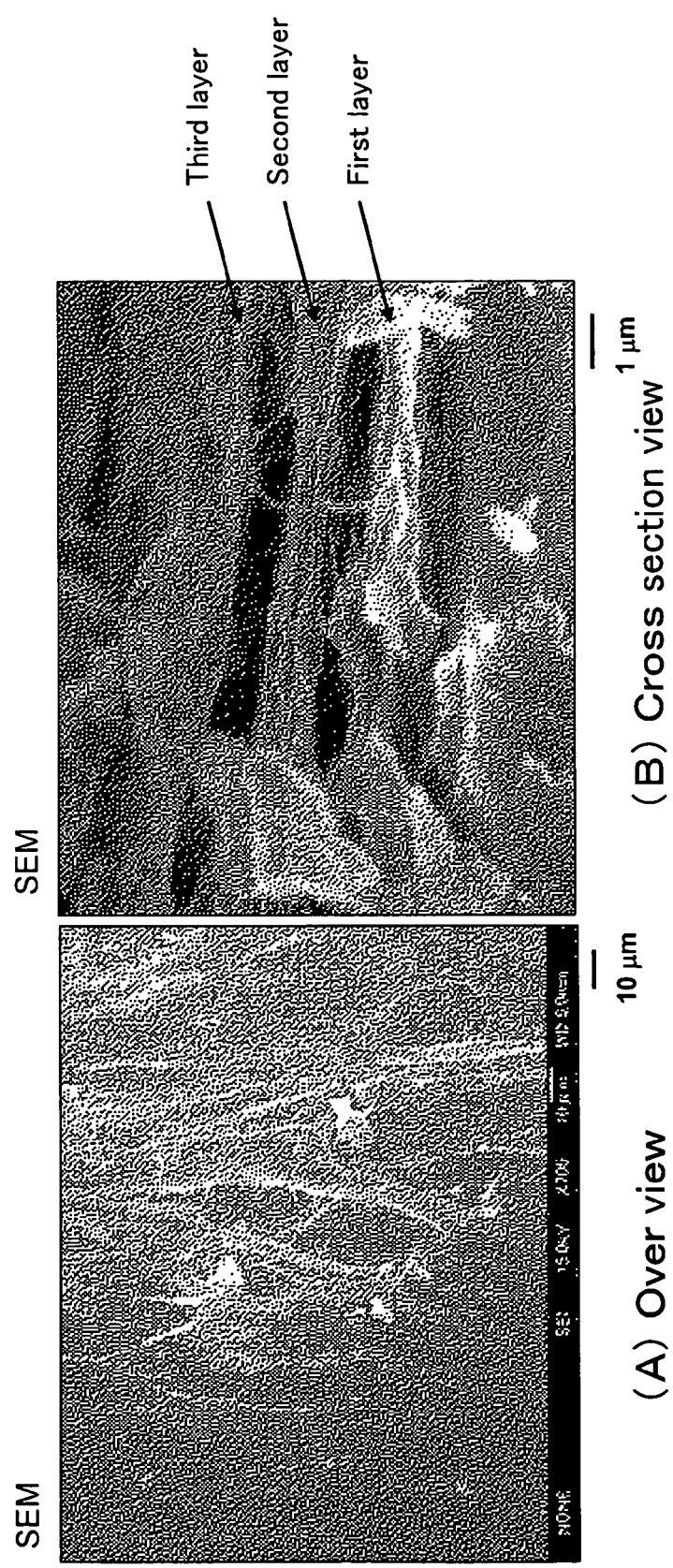
FIG. 7 shows SEM images of a three-dimensional tissue obtained in still another example of the present invention.

The surface of the thus-obtained three-dimensional tissue was observed with a SEM. The result is shown in the SEM images of FIG. 7. In FIG. 7, the SEM image (A) shows the surface of the three-dimensional tissue and the SEM image (B) shows the cross section of the three-dimensional tissue.

The three-dimensional tissue was subjected to actin staining with phalloidin-rhodamine and then observed with a confocal fluorescence microscope. The result is shown in the micrographs of FIG. 8.

As shown in FIG. 7, in Example 4, the lamination of UASMCs in the height direction became possible by providing the nano-ECMs intervening between each pair of the adjacent cell layers. Moreover, as a result of the actin staining, it was found that, in Example 4, the cells were laminated in the height direction as shown in the micrograph (A) of FIG. 8 and the cells also were laminated in the same direction within the plane as shown in the micrograph (B) of FIG. 8.

EXAMPLE 5

Formation of nano-ECMs and culture of human umbilical artery smooth muscle cells (UASMCs) were performed alternately on a slide glass in the same manner as in Example 4, thus forming a three-dimensional tissue having a layered structure composed of first nano-ECM/first cell layer/second nano-ECM/second cell layer/third nano-ECM/third cell layer/fourth nano-ECM/fourth cell layer. The formation of the fourth nano-ECM and the culture of the fourth cell layer were performed in the same manners as those for the third nano-ECM and the third cell layer, respectively.

Figure 9:
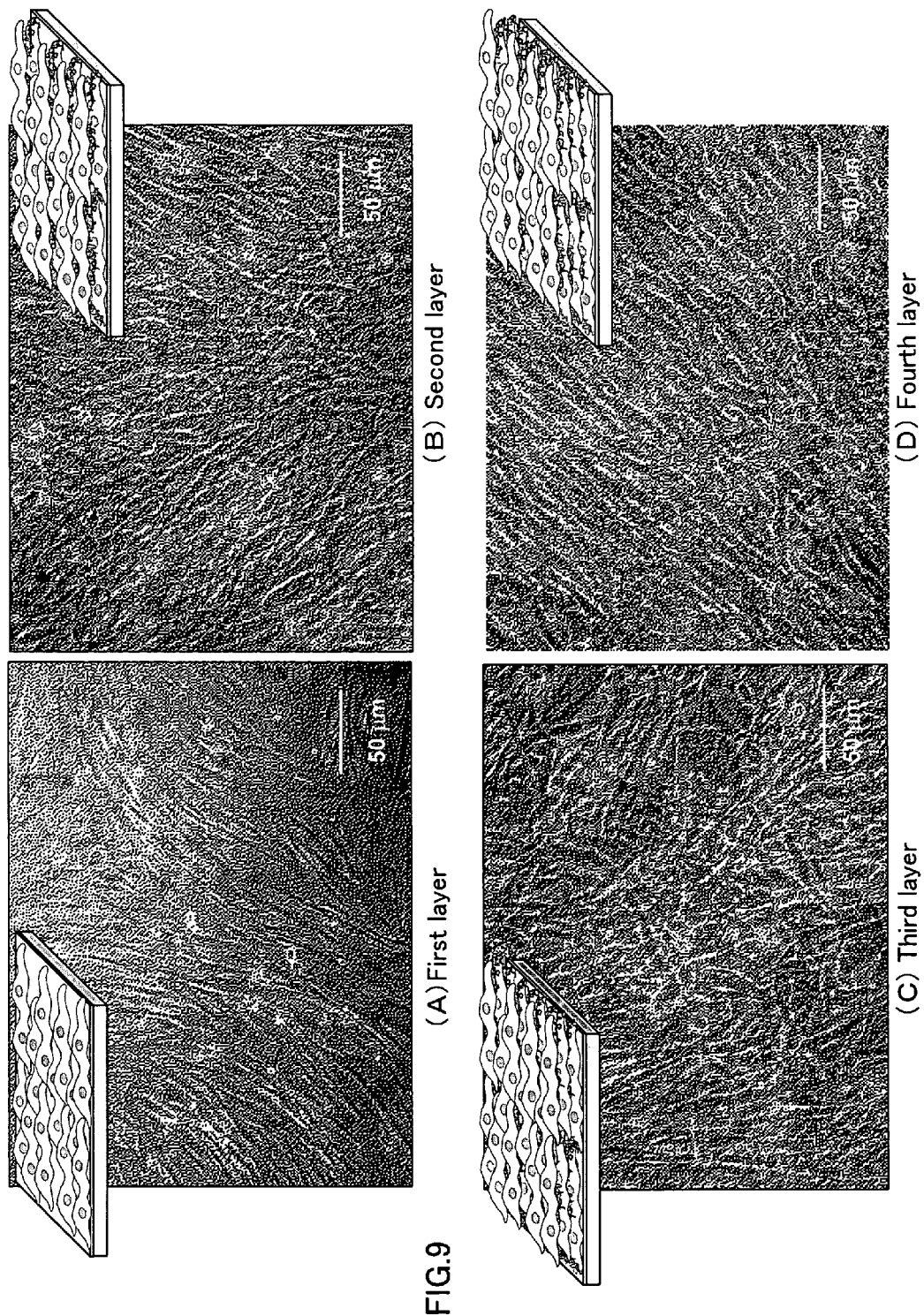
FIG. 9 shows phase-contrast micrographs of a three-dimensional tissue obtained in still another example of the present invention.

The respective cell layers were observed with a phase-contrast microscope prior to the subsequent nano-ECM formation. The results are shown in FIG. 9. In FIG. 9, the micrograph (A) shows an image of a first cell layer, the micrograph (B) shows an image of a second cell layer, the micrograph (C) shows an image of a third cell layer, and the micrograph (D) shows an image of a fourth cell layer. Each of the micrographs is accompanied by a schematic view showing the state of the cell lamination.

As shown in FIG. 9, it was found that the cell lamination proceeded in the height direction as the steps were repeated.

EXAMPLE 6

A nano-ECM composed of gelatin and fibronectin and a nano-ECM composed of gelatin and laminin were produced, respectively. The substrate used for the nano-ECM formation was a quartz crystal microbalance (QCM) substrate, and the thickness of the matrix being formed was determined by measuring a frequency shift.

(1) Nano-ECM Composed of Gelatin-Fibronectin

A nano-ECM in which gelatin and fibronectin are laminated alternately was formed on the QCM substrate in the same manner as in Example 1, except that a 0.05 M Tris buffer (pH 7.4) containing 1 mg/ml (0.1 wt %) gelatin and 0.15 M NaCl was used as the gelatin-containing buffer and a 0.05 M Tris buffer (pH 7.4) containing 0.2 mg/ml (0.02 wt %) fibronectin and 0.15 M NaCl was used as the fibronectin-containing buffer. The frequency shifts measured in the respective steps during the formation of this nano-ECM are shown in the graph of FIG. 10A. In FIG. 10A, an open circle indicates the result obtained after the dipping in the gelatin-containing buffer, and a filled circle indicates the result obtained after the dipping in the fibronectin-containing buffer ("a" in FIG. 10A). The thickness of the nano-ECM was about 10 nm after the two dipping steps and was about 13 nm after the eight dipping steps.

(2) Nano-ECM Composed of Gelatin-Laminin

A nano-ECM in which gelatin and laminin are laminated alternately was formed on the QCM substrate by dipping the QCM substrate in the same manner as in the above, except that a 0.05 M Tris buffer (pH7.4) containing 0.1 wt % laminin and 0.15 M NaCl was used instead of the fibronectin-containing buffer. The frequency shifts measured in the respective steps during the formation of this nano-ECM also are shown in the graph of FIG. 10A. In FIG. 10A, an open square indicates the result obtained after the dipping in the gelatin-containing buffer, and a filled square indicates the result obtained after the dipping in the laminin-containing buffer ("b" in FIG. 10A).

Figure 10B:
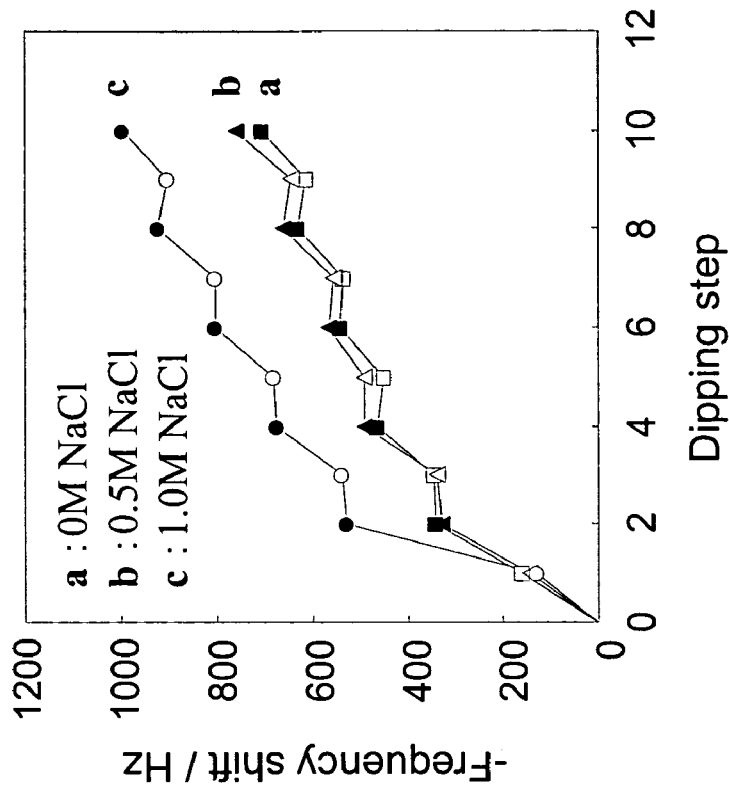
FIG. 10 is a graph showing the relationship between a frequency shift and the number of dipping steps performed in still another example of the present invention.
Figure 10A:
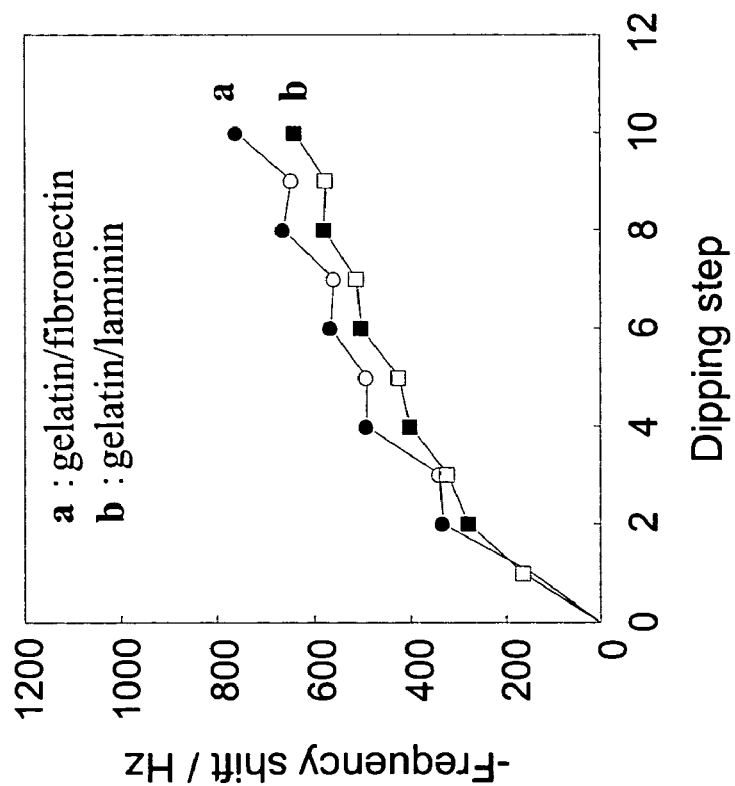

As shown in FIGS. 10A and 10B, the frequency shift decreased as the steps were repeated, which demonstrates that nanoscale layers were formed successively on the QCM substrate. Furthermore, the fact that the decrease in the frequency correlated with the number of steps teaches that the thickness of a nano-ECM to be formed can be increased by increasing the number of steps and can be decreased by decreasing the number of steps.

(3) Influence of NaCl

Nano-ECMs in which gelatin and fibronectin are laminated alternately were formed in the same manner as described in the section (1) above, except that the NaCl concentrations in the gelatin-containing buffer and the fibronectin-containing buffer were set to predetermined values (0 M, 0.15 M, and 1.0 M). The frequency shifts measured in the respective steps during the formation of these nano-ECMs are shown in FIG. 10B. In FIG. 10B, an open square and a filled square indicate the results obtained when the NaCl concentration was 0 M ("a" in FIG. 10B), an open triangle and a filled triangle indicate the results obtained when the NaCl concentration was 0.15 M ("b" in FIG. 10B), and an open circle and a filled circle indicate the results obtained when the NaCl concentration was 1.0 M ("c" in FIG. 10B), and all the open symbols (the open square, the open triangle, and the open circle) indicate the results obtained after the dipping in the gelatin-containing buffer, and all the filled symbols (the filled square, the filled triangle, and the filled circle) indicate the results obtained after the dipping in the fibronectin-containing buffer.

As shown in FIG. 10B, the frequency decreased as the NaCl concentration in the buffer increased, which demonstrates that the thickness of the nano-ECM being formed increased. From this fact, it can be said that the thickness of the nano-ECM can be adjusted by adjusting the concentration of a salt such as NaCl.

(4) Stability of Nano-ECM

Figure 11:
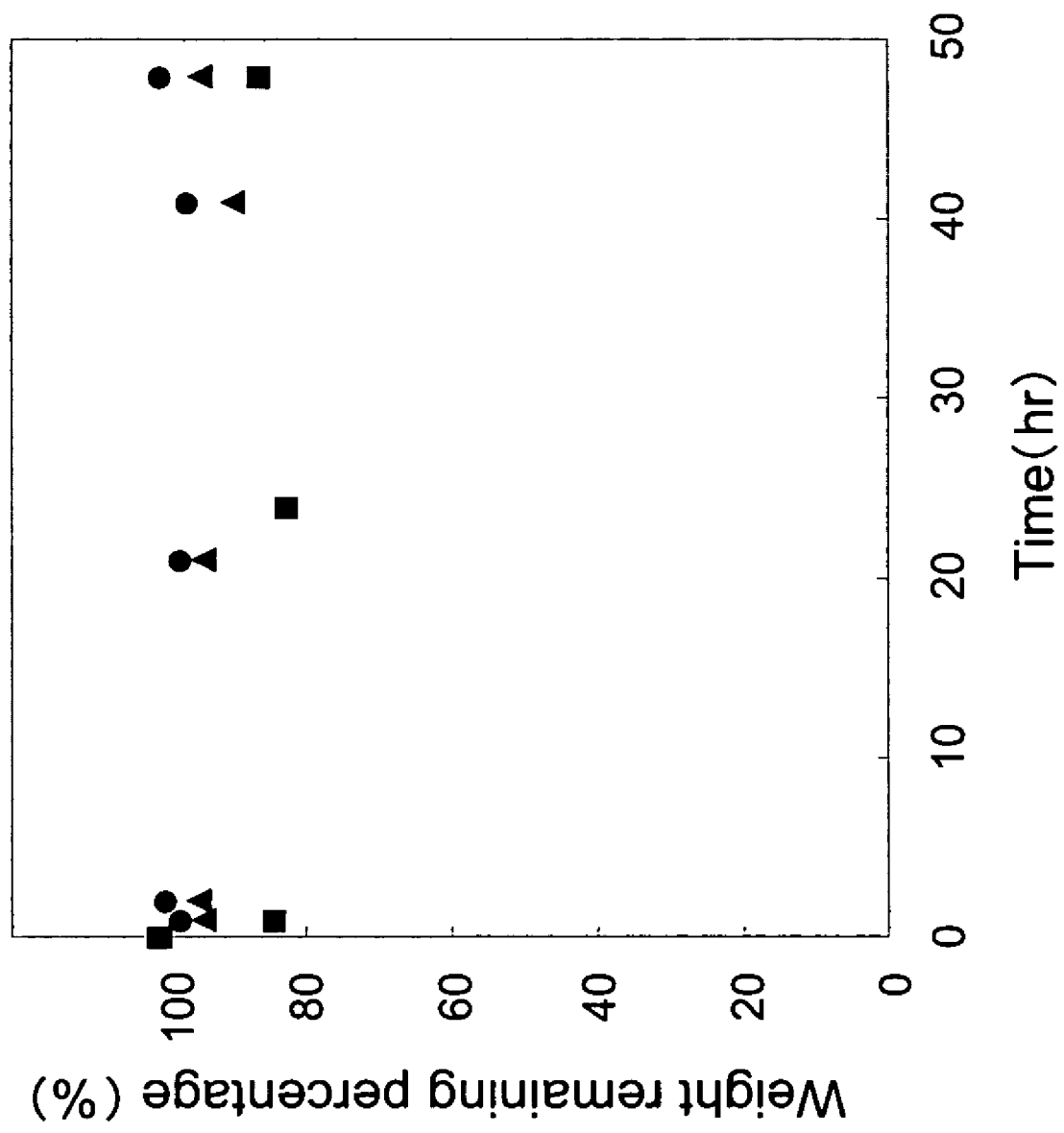
FIG. 11 is a graph showing the change in amount of a remaining ECM over time in still another example of the present invention.

A nano-ECM was formed on a QCM substrate by dipping the QCM substrate in the gelatin-containing buffer and the fibronectin-containing buffer in the same manner as described in the section (3) above so that the ten dipping steps were performed in total. Then, the QCM substrate provided with the nano-ECM was dipped in Eagle's MEM containing 10 wt % FBS, and the stability of the nano-ECM in the medium was examined. The stability was evaluated by measuring the change in frequency of the QCM substrate over time and calculating the amount (weight: %) of the remaining nano-ECM. Note here that the amount (%) of the remaining nano-ECM was determined by calculating a relative ratio of the measured frequency with respect to the frequency before being dipped in the culture medium as 100%. The result is shown in FIG. 11. In FIG. 11, a filled square indicates the result obtained when the NaCl concentration was 0 M, a filled triangle indicates the result obtained when the NaCl concentration was 0.15 M, and a filled circle indicates the result obtained when the NaCl concentration was 1.0M.

As shown in FIG. 11, the weight of the nano-ECM did not change substantially after it had been dipped in the culture medium. The same experiment was conducted with respect to nano-ECMs with different thicknesses, and it was found that the nano-ECMs were all stable in the culture medium. These results demonstrate that the thickness of the nano-ECM does not affect the stability of the nano-ECM in the culture medium.

Industrial Applicability

As specifically described above, according to the ECM production method of the present invention, a nanoscale-thick ECM for adhering cell layers can be produced merely by bringing a cell layer into contact with a first substance-containing solution and a second substance-containing solution alternately. Thus, according to the three-dimensional tissue production method of the present invention that uses this ECM production method, merely by repeating the step of forming a cell layer and the step of bringing the cell layer into contact with a first substance-containing solution and a second substance-containing solution alternately, it is possible to laminate a plurality of cell layers successively with a nanoscale-thick ECM intervening between each pair of the adjacent cell layers. Thus, unlike the conventional methods, the method according to the present invention does not require separating a single cell sheet, laminating a plurality of separated cell sheets, etc., so that the three-dimensional tissue can be produced with excellent reproducibility and efficiency in a very simple manner. Therefore, the three-dimensional tissue production method according to the present invention is particularly useful for reconstruction of tissues having a complex three-dimensional structure and thus is a very useful technique in the field of regenerative medicine.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A method of producing a three-dimensional tissue by cell lamination, the method comprising the steps of:
    (A) forming a cell layer;
    (B) bringing the cell layer into contact with a solution containing a first substance and a solution containing a second substance alternately, thus forming, on the cell layer, an extracellular matrix having a thickness of 1 to 100 nm in which the first substance and the second substance are laminated alternately;
    (C) culturing cells on the extracellular matrix to form a cell layer; and
    (D) repeating the steps (B) and (C) at least once,
    wherein in the step (A), the cell layer is formed on a substrate,
    in the step (D), the cell layer of the step (B) is formed on the extracellular matrix in the step (C),
    a combination of the first substance and the second substance is a combination of a protein having an RGD sequence and a protein that interacts with the protein having the RGD sequence,
    pH of the solution containing the first substance is 6 or more and 8 or less,
    pH of the solution containing the second substance is 6 or more and 8 or less,
    the step (B) is conducted after the step (A) or (C), and
    the step (C) is conducted after the step (B).

2. The method according to claim 1, wherein the first substance is at least one selected from the group consisting of fibronectin, vitronectin, laminin, cadherin, and collagen, and the second substance is at least one selected from the group consisting of gelatin, albumin, globulin, and elastin.

3. The method according to claim 1, wherein the first substance is fibronectin or laminin.

4. The method according to claim 3, wherein the combination of the first substance and the second substance is a combination of fibronectin and gelatin or a combination of laminin and gelatin.

5. The method according to claim 1, wherein, in the step (B), the cell layer is brought into contact with the solution containing the first substance first to form a first substance layer as a lowermost layer of the extracellular matrix.

6. The method according to claim 1, wherein, in the step (B), the cell layer is brought into contact with the solution containing the first substance last to form a first substance layer as an uppermost layer of the extracellular matrix.

7. The method according to claim 1, further comprising, prior to the step (A), the step of bringing the substrate into contact with the solution containing the first substance and the solution containing the second substance alternately, thus forming, on the substrate, an extracellular matrix in which the first substance and the second substance are laminated alternately,
    wherein, in the step (A), the cell layer is formed on the extracellular matrix formed on the substrate.

8. The method according to claim 7, wherein the extracellular matrix having a thickness of at least 1 nm is formed on the substrate.

9. The method according to claim 7, wherein the substrate is brought into contact with the solution containing the first substance last to form a first substance layer as an uppermost layer of the extracellular matrix formed on the substrate.

10. The method according to claim 1, wherein the cell is at least one cell selected from the group consisting of a hepatocyte, a vascular endothelial cell, a fibroblast, an epidermic cell, an epithelial cell, a mammary glandular cell, a myocyte, a neurocyte, a tissue stem cell, an embryonic stem cell, a bone cell, and an immunocyte.

11. The method according to claim 1, wherein at least one of the solution containing the first substance and the solution containing the second substance further contains at least one substance selected from the group consisting of cell growth factors, cytokines, chemokines, hormones, and biologically active peptides.

12. The method according to claim 1, wherein at least one of the solution containing the first substance and the solution containing the second substance further contains at least one substance selected from the group consisting of therapeutic agents for treating diseases, prophylactic agents for preventing diseases, and inhibitors for inhibiting diseases.

13. A method of producing an extracellular matrix for adhering cell layers, the method comprising the step of:
bringing a cell layer into contact with a solution containing a first substance and a solution containing a second substance alternately, thus forming, on the cell layer, a thin film having a thickness of 1 to 100 nm in which the first substance and the second substance are laminated alternately as an extracellular matrix,
wherein a combination of the first substance and the second substance is a combination of a protein having an RGD sequence and a protein that interacts with the protein having the RGD sequence,
pH of the solution containing the first substance is 6 or more and 8 or less, and
pH of the solution containing the second substance is 6 or more and 8 or less.

14. The method according to claim 13, wherein the cell layer is formed on a substrate by culturing a cell on the substrate.

15. The method according to claim 13, wherein the first substance is at least one selected from the group consisting of fibronectin, vitronectin, laminin, cadherin, and collagen, and the second substance is at least one selected from the group consisting of gelatin, albumin, globulin, and elastin.

16. The method according to claim 1, wherein contacting of the cell layer with the respective solutions in the step (B) is dipping the cell layer in the respective solutions, or dripping or spraying the respective solutions on the cell layer.

17. The method according to claim 13, wherein contacting of the cell layer with the respective solutions is dipping the cell layer in the respective solutions, or dripping or spraying the respective solutions on the cell layer.

* * * * *